(12) United States Patent
Roby

(10) Patent No.: US 6,878,757 B2
(45) Date of Patent: Apr. 12, 2005

(54) ANTIMICROBIAL SUTURE COATING

(75) Inventor: Mark Roby, Killingworth, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 10/729,677

(22) Filed: Dec. 5, 2003

(65) Prior Publication Data

US 2004/0147629 A1 Jul. 29, 2004

Related U.S. Application Data

(60) Provisional application No. 60/432,708, filed on Dec. 11, 2002.

(51) Int. Cl.$^7$ ............................ C08G 63/68; B32B 27/34
(52) U.S. Cl. ...................... 523/122; 428/364; 428/378; 428/394; 428/395; 528/295; 606/1.151; 606/228; 606/230; 606/231
(58) Field of Search ............................ 606/1.151, 228, 606/230, 231; 428/364, 378, 394, 395; 523/122; 528/295

(56) References Cited

U.S. PATENT DOCUMENTS

| | | | |
|---|---|---|---|
| 4,027,676 A | 6/1977 | Mattei | |
| 4,043,344 A | 8/1977 | Landi et al. | |
| 4,047,533 A | 9/1977 | Perciaccante et al. | |
| 4,080,969 A | 3/1978 | Casey et al. | |
| 4,705,820 A | 11/1987 | Wang et al. | |
| 4,711,241 A | 12/1987 | Lehmann | |
| 5,032,638 A | 7/1991 | Wang et al. | |
| 5,123,912 A | 6/1992 | Kaplan et al. | |
| 5,716,376 A | 2/1998 | Roby et al. | |
| 6,017,553 A | 1/2000 | Burrell et al. | |
| 6,183,499 B1 * | 2/2001 | Fischer et al. | 606/228 |
| 6,267,782 B1 * | 7/2001 | Ogle et al. | 623/1.1 |

* cited by examiner

*Primary Examiner*—Kriellion A. Sanders

(57) ABSTRACT

Compositions with antimicrobial properties contain a fatty acid ester salt mixed with a bioabsorbable copolymer. These compositions are useful in forming coatings for surgical articles, including multifilament sutures.

22 Claims, 1 Drawing Sheet

ANTIMICROBIAL SUTURE COATING

This application claims priority from Provisional Application Ser. No. 60/432,708 filed on Dec. 11, 2002.

BACKGROUND

1. Technical Field

Coated surgical sutures having improved antimicrobial properties and a method for using these sutures are described. More particularly, surgical sutures coated with fatty acid esters such as sodium stearoyl lactylate and/or other non-silver stearoyl lactylates in an effective antimicrobial amount are described herein.

2. Background of Related Art

Synthetic absorbable multifilament sutures are well known in the industry. Examples of these sutures include Dexon, Vicryl, and Polysorb, commercially available from Ethicon, Inc. (Somerville, N.J.), and United States Surgical Corporation (Norwalk, Conn.).

It is known that suture materials are often coated with various substances to improve their handling characteristics. For example, U.S. Pat. Nos. 5,123,912, 4,080,969, 4,043,344, 4,047,533, and 4,027,676 disclose coated surgical sutures with improved knot tie down properties.

Suture coatings containing esters of fatty acids are also known. For example, U.S. Pat. No. 5,716,376 discloses suture coatings made of a mixture of fatty acid esters, including calcium stearoyl lactylate, with a copolymer containing caprolactone. The coatings taught by this patent are used for absorbable sutures and other surgical articles and, in the case of sutures, impart improved properties to the suture, such as knot security, surgeon's throw, lubricity, knot run down, and/or knot repositioning. U.S. Pat. No. 4,711,241 discloses suture coatings that include oleyl lactylates containing alkaline earth ions or radicals, with a preferred embodiment consisting of calcium stearoyl-2-lactylate. U.S. Pat. No. 5,032,638 discloses a suture coating comprising a copolymer of poly (Beta-hydroxybutyrate) and a stearoyl lactylate containing alkaline-earth metals, and notes that calcium stearoyl lactylate and magnesium stearoyl lactylate can be added as lubricants. Similarly, U.S. Pat. No. 4,705,820 discloses a suture coating comprising a random copolymer and a lubricant, which can be a stearoyl lactylate.

It is also known to coat medical articles, including sutures, with metallic compounds to impart antimicrobial characteristics to the articles. The anti-microbial effects of metallic ions including Ag, Au, Pt, Pd, Ir, Cu, Sn, Sb, Bi and Zn are known (see Morton, H. E., Pseudomonas in Disinfection, Sterilization and Preservation, ed. S. S. Block, Lea and Febiger, 1977 and Grier, N., Silver and Its Compounds in Disinfection, Sterilization and Preservation, ed. S. S. Block, Lea and Febiger, 1977). Silver is one of the preferred metallic ions, due to its unusually good bioactivity at low concentrations. In modern medical practice both inorganic and organic soluble salts of silver are used to prevent and treat microbial infections. While these compounds are effective as soluble salts, they do not provide prolonged protection and must be frequently reapplied. Reapplication may not always be practical, especially where an implanted device is involved. U.S. Pat. No. 6,017,553 attempts to improve upon the use of silver as an antimicrobial agent for medical devices by creating atomic disorder during vapor deposition of the metallic antimicrobial agents.

Sutures having antimicrobial properties, that are inexpensive and can be constructed with biocompatible materials without being subject to excessive diffusion, are still desirable. This is especially so where the suture is absorbable and there is no opportunity to reapply the antimicrobial coating.

SUMMARY

It has now been found that an antimicrobial coating for absorbable surgical articles may be formed from the mixture of a bioabsorbable polymer, such as, for example, a copolymer containing caprolactone, with an effective antimicrobial amount of an ester of a fatty acid. An "effective antimicrobial amount" of a given component is an amount at which the component hinders the growth of bacteria associated with infections, and promotes the healing of a wound.

Preferably, mixtures useful in forming the aforementioned coatings include an ester of a fatty acid as a predominant component in an effective antimicrobial amount. A "predominant component" is a component which is present in an amount greater than about 50 weight percent. A "minor component" is a component which is present in an amount up to about 50 weight percent. The minor component comprises copolymers containing caprolactone.

Particularly useful caprolactone containing copolymers are branched or "star" copolymers obtained by polymerizing a major amount of epsilon-caprolactone and a minor amount of another bioabsorbable monomer polymerizable therewith in the presence of a polyhydric alcohol initiator.

Preferably, the antimicrobial absorbable coating composition for surgical sutures is inexpensive, biocompatible, and not subject to excessive diffusion. In a particularly useful embodiment, the antimicrobial absorbable coating composition is applied to multifilament synthetic surgical sutures.

Particularly useful fatty acid esters used as the antimicrobial agent are non-silver stearoyl lactylates. In a particularly preferred embodiment, the fatty acid ester used as the antimicrobial agent is sodium stearoyl lactylate. In another embodiment, the fatty acid esters used as the antimicrobial agent may be combined with silver stearoyl lactylate.

DESCRIPTION OF THE PREFERRED EMBODIMENTS

Figure 1:
FIG. 1 is a perspective view of a coated suture attached to a needle described herein.

It has been found that fatty acid esters and bioabsorbable polymers, especially those containing caprolactone, can advantageously be mixed to form a composition (with fatty acid esters as the predominant component thereof) useful in coating surgical sutures to impart antimicrobial characteristics to the sutures.

Any bioabsorbable polymer known to those skilled in the art can be employed in the present coatings. In particularly useful embodiments, the bioabsorbable polymer contains epsilon-caprolactone as a component thereof Suitable caprolactone containing copolymers include copolymers which may be synthesized by well known conventional polymerization techniques; see, for example Principles of polymerization, George Odian, III Edition; 1991 pp.569–573, the contents of which are incorporated herein by reference.

Preferably, the caprolactone containing copolymer is obtained by polymerizing a major amount of epsilon-caprolactone and a minor amount of at least one other copolymerizable monomer or mixture of such monomers in the presence of a polyhydric alcohol initiator to produce a branched copolymer. The polymerization of these monomers contemplates all of the various types of monomer addition, i.e., simultaneous, sequential, simultaneous followed by sequential, sequential followed by simultaneous, etc.

The copolymer herein can contain from about 70 to about 98, and preferably from about 80 to about 95, weight percent epsilon-caprolactone derived units, the balance of the copolymer-being derived from the other copolymerizable monomer(s).

Suitable monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including both alpha hydroxy acids (such as glycolic acid and lactic acid) and beta hydroxyacids (such as beta hydroxybutyric acid and gamma hydroxyvaleric acid); polyalkyl ethers (such as polyethylene glycol and polyloropyline glycol and combinations thereof); with glycolide being a preferred monomer.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in small amounts, e.g., from about 0.01 to about 5, and preferably from about 0.1 to about 3, weight percent of the total monomer mixture.

The coating composition can contain from about 0.3 to about 10, and preferably from about 0.5 to about 5, weight percent of the absorbable polymer.

Suitable fatty acid esters which can be used in the present coatings include esters of the formula:

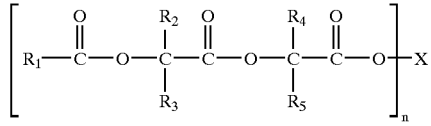

wherein x is a metal other than silver, an alkaline-earth metal, alkali metal, or ions thereof and $R_1$ is $C_{10}$ or greater alkyl, $R_2$ is H, or $C_1$–$C_3$ alkyl, $R_3$ is H, or $C_1$–$C_3$ alkyl, $R_4$ is H, or $C_1$–$C_3$ alkyl, $R_5$ is H, or $C_1$–$C_3$ alkyl, and n>1. Such suitable fatty acids include sodium, lithium, potassium, rubidium, cesium or francium stearoyl lactylate; sodium, lithium, potassium, rubidium, cesium or francium palmityl lactylate; sodium, lithium, potassium, rubidium, cesium or francium olelyl lactylate; with sodium stearoyl lactylate being preferred.

The fatty acid esters are present in the coating composition in an effective antimicrobial amount as defined above. Typically, the fatty acid esters will be present in an amount from about 30 percent to about 70 percent by weight of the coating composition. Preferably, the fatty acid ester is present in an amount from about 45 percent to about 55 percent by weight of the coating composition.

The caprolactone containing copolymer and the fatty acid ester are non-toxic; a mixture of the two is non-toxic as well. In alternative embodiments, a silver stearoyl lactylate is combined with the fatty acid ester in the coating composition.

The bioabsorbable mixture herein can be applied to a suture by any suitable process, e.g., passing the suture through a solution of the copolymer, e.g., in toluene, methylene chloride, etc., past a brush or other coating solution applicator, or past one or more spray nozzles dispensing the suture coating solution. The coating solution can contain from about 80 to about 99.9, preferably from about 90 to about 98, more preferably from about 94 to about 97 weight percent solvent. In a preferred embodiment, a mixture of methylene chloride, hexane and ethanol is used as a solvent. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

While the coating composition herein can be applied to any type of suture, it is essentially intended for application to a braided suture, a preferred type of which is disclosed in U.S. Pat. No. 5,019,093. The amount of coating composition applied to a braided suture will vary depending upon the structure of the suture, e.g., the number of filaments, tightness of braid or twist, the size of the suture and its composition. Suitable coating levels range from about 0.3% to about 10% with about 0.5% to about 5% being preferred.

The coated suture 101 may be attached to a surgical needle 100 as shown in FIG. 1 by methods well known in the art. Wounds may be sutured by passing the needled suture through tissue to create wound closure. The needle preferably is then removed from the suture and the suture tied. The coating advantageously possesses antimicrobial properties to promote healing and prevent infection.

It will be understood that various modifications may be made to the embodiments disclosed herein. For example, although it is preferred to coat surgical sutures from the disclosed mixtures, a wide variety of surgical articles can be coated. These include but are not limited to clips and other fasteners, staples, pins, screws, prosthetic devices, drug delivery devices, meshes or fabrics, anastomosis rings, and other implantable devices. Therefore, the above description should not be construed as limiting, but merely as exemplifications of preferred embodiments. Those skilled in the art will envision other modifications within the scope and spirit of the claims appended hereto.

What is claimed is:

1. A surgical suture coating comprising:
   a) a copolymer comprising a predominant amount of epsilon-caprolactone and a minor amount of at least one other copolymerizable monomer; and
   b) an effective antimicrobial amount of a fatty acid ester salt selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

2. The surgical suture coating of claim 1 wherein silver stearoyl lactylate is combined with said fatty acid ester salt.

3. The surgical suture coating of claim 1 wherein the surgical suture coating comprises from about 0.3 to about 10 percent by weight of the copolymer and from about 30 to about 70 percent by weight of the fatty acid ester salt.

4. A surgical suture coating comprising:
a) a copolymer comprising a predominant amount of epsilon-caprolactone and a minor amount of at least one other copolymerizable monomer; and
b) an effective antimicrobial amount of sodium stearoyl lactylate.

5. The surgical suture coating of claim 4 wherein silver stearoyl lactylate is combined with the sodium stearoyl lactylate.

6. A surgical suture comprising one or more filaments of bioabsorbable material coated with a composition that includes an effective antimicrobial amount of sodium stearoyl lactylate.

7. The surgical suture of claim 6, wherein the suture is a braided suture.

8. The surgical suture of claim 6 wherein silver stearoyl lactylate is combined with the sodium stearoyl lactylate.

9. The surgical suture of claim 6 wherein one or more filaments of bioabsorbable material are coated with a composition comprising from about 0.3 to about 10 percent by weight of a branched copolymer containing a major amount of epsilon-caprolactone and a minor amount of at least one other copolymerizable monomer.

10. The surgical suture of claim 9 wherein the other copolymerizable monomer is selected from the group consisting of alkylene carbonates, dioxanones, dioxepanones, absorbable cyclic amides, absorbable cyclic ether-esters derived from crown ethers, hydroxyacids capable of esterification, polyalkyl ethers, and combinations thereof.

11. The surgical suture of claim 10 wherein the other copolymerizable monomer is selected from the group consisting of glycolide, lactide, p-dioxanone and trimethylene carbonate.

12. The surgical suture of claim 9 wherein the composition comprises from about 80 to about 95 weight percent epsilon-caprolactone.

13. A method of suturing a wound comprising:
a) providing a sterilized needled suture, said suture being coated with a composition comprising a mixture of:
1) a copolymer comprising the reaction product obtained by polymerizing a major amount of epsilon-caprolactone and a minor amount of at least one other copolymerizable monomer selected from the group consisting of alkylene carbonates, dioxanones, dioxepanones, absorbable cyclic amides, absorbable cyclic ether-esters derived from crown ethers, hydroxyacids capable of esterification, polyalkyl ethers, and combinations thereof, in the presence of polyhydric alcohol as initiator; and
2) an effective antimicrobial amount of a fatty acid ester salt selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate; and
b) passing said needled suture through tissue to create wound closure.

14. The method of claim 13 wherein silver stearoyl lactylate is combined with said fatty acid ester.

15. A method of suturing a wound comprising:
a) providing a sterilized needled suture, said suture being coated with a composition comprising a mixture of:
1) a copolymer comprising the reaction product obtained by polymerizing a major amount of epsilon-caprolactone and a minor amount of at least one other copolymerizable monomer selected from the group consisting of alkylene carbonates, dioxanones, dioxepanones, absorbable cyclic amides, absorbable cyclic ether-esters derived from crown ethers, hydroxyacids capable of esterification, polyalkyl ethers, and combinations thereof, in the presence of polyhydric alcohol as initiator; and
2) an effective antimicrobial amount of sodium stearoyl lactylate; and
b) passing said needled suture through tissue to create wound closure.

16. The method of claim 15 wherein silver stearoyl lactylate is combined with said sodium stearoyl lactylate.

17. An article comprising an implantable medical device having a coating comprising a mixture of:
a) a copolymer comprising a predominant amount of epsilon-caprolactone and a minor amount of glycolide; and
b) an amount of a fatty acid ester salt sufficient to hinder the growth of bacteria associated with infections, the fatty acid ester salt being selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, francium olelyl lactylate.

18. The implantable medical device of claim 17 wherein silver stearoyl lactylate is combined with said fatty acid ester.

19. The implantable medical device of claim 17 wherein said medical device is selected from the group consisting of clips, staples, pins, screws, prosthetic devices, anastomosis rings, and growth matrices.

20. An article comprising an implantable medical device having a coating comprising a mixture of:
a) a copolymer comprising a predominant amount of epsilon-caprolactone and a minor amount of glycolide; and
b) an effective antimicrobial amount of sodium stearoyl lactylate.

21. The implantable medical device of claim 20 wherein silver stearoyl lactylate is combined with said sodium stearoyl lactylate.

22. The implantable medical device of claim 20 wherein said medical device is selected from the group consisting of clips, staples, pins, screws, prosthetic devices, anastomosis rings, and growth matrices.

\* \* \* \* \*